US006984752B2

(12) United States Patent
Jackson et al.

(10) Patent No.: US 6,984,752 B2
(45) Date of Patent: Jan. 10, 2006

(54) PROCESS FOR PREPARING VINYL PHOSPHONIC ACID

(75) Inventors: Richard David Jackson, Worcestershire (GB); Kevin Roger Kenneth Matthews, Warwickshire (GB)

(73) Assignee: Rhodia Consumer Specialties Limited, Watford (GB)

( * ) Notice: Subject to any disclaimer, the term of this patent is extended or adjusted under 35 U.S.C. 154(b) by 50 days.

(21) Appl. No.: 10/486,228

(22) PCT Filed: Aug. 2, 2002

(86) PCT No.: PCT/GB02/03573

§ 371 (c)(1),
(2), (4) Date: Mar. 5, 2004

(87) PCT Pub. No.: WO03/016319

PCT Pub. Date: Feb. 27, 2003

(65) Prior Publication Data

US 2004/0249194 A1    Dec. 9, 2004

(30) Foreign Application Priority Data

Aug. 15, 2001   (GB)   .................................... 0119885

(51) Int. Cl.
*C07F 8/28*   (2006.01)
(52) U.S. Cl. .......................................................... 562/8
(58) Field of Classification Search ..................... 562/8
See application file for complete search history.

(56) References Cited

U.S. PATENT DOCUMENTS 4,518,745 A * 5/1985 Engelhardt et al. ...... 525/326.6

FOREIGN PATENT DOCUMENTS

EP           0 065 739 A     12/1982
WO         WO 92 02524 A     2/1992

OTHER PUBLICATIONS

Qiao et al.: "Synthesis of a C-phosphate disaccharide as a potential inhibitor of peptidoglycan polymerization by trans-glycosylase", Journal of Organic Chemistry, vol. 58, No. 13, 1993, pp. 3480-3482, XP002221483 American Chemical Society, Easton., US ISSN: 0022-3263, p. 3481, scheme I, preparation of compound 14.

Hernandez-Laguna et al.: "Electronic structure and conformational properties of vinylphosphonic acid and some related derivatives", Journal of Physical Chemistry, vol. 98, No. 4, 1994, pp. 1109-1116, XP008009963, American Chemical Society, US ISSN: 0022-3654, p. 1110, paragraph 3.2.

* cited by examiner

Primary Examiner—Johann Richter
Assistant Examiner—Chukwuma Nwaonicha
(74) Attorney, Agent, or Firm—Frishauf, Holtz, Goodman & Chick, P.C.

(57) ABSTRACT

Vinyl phosphonic acid is produced by the hydrolysis of a vinyl phosphonic acid ester (e.g. "Bis Beta") in the presence of a carbonyl compound (e.g. a monofunctional or difunctional aldehyde or a ketone).

22 Claims, No Drawings

PROCESS FOR PREPARING VINYL PHOSPHONIC ACID

This application is a U.S. National Phase Application under 35 USC 371 of International Application PCT/GB02/03573 filed Aug. 2, 2002.

This invention relates to the production of vinyl phosphonic acid and in particular to the production of vinyl phosphonic acid by hydrolysis of a corresponding ester.

Vinyl phosphonic acid is a useful ingredient in the production of flame-retardant agents. Polymers of vinyl phosphonic acid can be used in paints, plastics materials and corrosion inhibitors, amongst others.

It is known to produce vinyl phosphonic acid by hydrolysis of a corresponding ester in the presence of an acidic or a basic catalyst. However, the product of such a hydrolysis has been found to be substantially impure and contaminated with alcohols and other organics.

We have discovered that hydrolysis of an ester (especially a halogenated ester) of vinyl phosphonic acid in the presence of a carbonyl compound (e.g. an aldehyde or a ketone) leads to the production of substantially pure vinyl phosphonic acid in good yield.

Although the present invention will be described herein with particular reference to the production of vinyl phosphonic acid by the hydrolysis of a bis (beta haloalkyl) ester of the acid, it is not to be construed as being limited thereto.

Accordingly, the present invention provides a method for the production of vinyl phosphonic acid, in which a vinyl phosphonic acid ester is hydrolysed in the presence of a carbonyl compound.

The present invention also provides vinyl phosphonic acid made by the method described in the immediately preceding paragraph.

In one embodiment of the present invention, the carbonyl compound may be a monofunctional aldehyde of general formula:

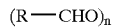

wherein R represents hydrogen or an alkyl group having from 1 to 10 carbon atoms and n is a whole number of 1 or greater.

The aldehyde may be, for example, formaldehyde, paraformaldehyde, metaformaldehyde or acetaldehyde.

In a second embodiment of the present invention, the carbonyl compound may be a difunctional aldehyde of general formula:

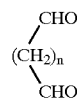

wherein n is zero or a whole number of from 1 to 4.

An example of such a difunctional aldehyde is glyoxal.

In a third embodiment of the present invention, the carbonyl compound may be a ketone of general formula:

wherein $R^1$ and $R^2$ (which may be the same or different) each represent an alkyl group having from 1 to 5 carbon atoms.

The ketone may, for example, be acetone.

Alternatively, the carbonyl compound may be a cycloalkyl ketone, for example, cyclohexanone.

Suitably, the ester which is to be hydrolysed is a bis(beta-haloalkyl) ester of vinyl phosphonic acid, preferably the bis(beta-chloroethyl) ester (hereinafter "BisBeta").

According to the present invention, the carbonyl compound is present in an amount of from 1 to 250 mole %, suitably from 50 to 200 mole % (with respect to the ester).

The hydrolysis is preferably carried out at a temperature of about 140°–150° C. and for a time of 30 to 40 hours.

The hydrolysis may be carried out at atmospheric pressure. Alternatively, the hydrolysis may be carried out at a pressure of up to 10 atmospheres (preferably from 1 to 4 atmospheres).

Suitably, the hydrolysis may be carried out under an inert (e.g. nitrogen) atmosphere.

The hydrolysis may conveniently be carried out in the presence of an initial acid catalyst (e.g. sulphuric acid or a heel of vinyl phosphonic acid) in an amount of from 1 to 10 mole % (with respect to the ester).

The present invention will be illustrated by way of the following examples:

In the examples, "Bisbeta" signifies the bis(beta-chloroethyl) ester of vinyl phosphonic acid and "VPA" signifies vinyl phosphonic acid itself.

EXAMPLE 1

A 5 liter flask fitted with stirrer, nitrogen inlet, condenser, thermometer, and addition tube (from peristaltic pump) was charged with BisBeta (5000 g, 21.45 mol) and VPA (231 g, 2.14 mol) and heated to 150° C. A 5% w/w solution of formaldehyde in water was then slowly fed in via the addition tube at a rate of approx 5 cm$^3$/min for 30–40 h. Distilled water was then fed in at the same rate for a further 6 h to remove residual formaldehyde and other volatiles. The final reaction mixture was then cooled to 100° C. and dried under reduced pressure to give VPA (92% by $^{31}$P nmr).

EXAMPLE 2 (COMPARATIVE EXAMPLE)

A 1 liter flask fitted with stirrer, nitrogen inlet, condenser, thermometer, and addition tube (from peristaltic pump) was charged with BisBeta (500 g, 2.14 mol) and VPA (34.8 g, 0.32 mol) and heated to 150° C. Water was then slowly fed in via the addition tube at a rate of approx. 5 cm$^3$/min for 30 to 40 h.

The final reaction mixture was then cooled to 100° C. and dried under reduced pressure to give VPA (78% by $^{31}$P nmr). The main impurities found in the VPA comprised ethylene glycol (shown to be present by $^{13}$C nmr).

EXAMPLE 3

A 1 liter flask fitted with stirrer, nitrogen inlet, thermometer, and addition tube (from peristaltic pump) was charged with BisBeta (500 g, 2.14 mol) and VPA (34.8 g, 0.32 mol) and heated to 150° C. Water was then slowly fed in via the addition tube at a rate of approx. 5 cm$^3$/min for 30–40 h. Paraformaldehyde (10 g, 0.33 mol) was then added as a solid and water was added at the same rate as above for a further 4 h. The reaction mixture was shown to be 87% VPA by $^{31}$P nmr.

It will be seen that VPA of improved purity was obtained when Example 3 was carried out on the final mixture of Example 2.

EXAMPLE 4

A 2 liter flask fitted with stirrer, nitrogen inlet, condenser, thermometer and addition tube (from peristaltic pump) was charged with BisBeta (2000 g, 8.58 mol) and VPA (92.7 g, 0.86 mol) and heated to 150° C. A 15% wt/wt solution of formaldehyde in water was slowly fed via the addition tube at a rate of 0.4 cm$^3$/min for 33 h. Distilled water was then fed in at 1.2 cm$^3$/min for 7 h to remove residual formaldehyde. The final reaction mixture was then cooled to 100° C. and dried under reduced pressure to give VPA (90% by $^{31}$P nmr).

EXAMPLE 5

Pilot Plant Scale

BisBeta (1600 kg, 6.86 kmol) and VPA (40 kg, 0.37 kmol) were charged to a 300 gallon reactor, set to condense and distil into a separate receiver. The system was pressurised to 1 bar (g) with nitrogen and maintained at that pressure. The mixture was heated to 140° C. and stirred. Steam (added through a sparge pipe at a rate of 50–70 kg/hr) and formaldehyde (1328 kg, 30% wt/wt; 13.28 kmol) were added, both over a period of 36 hours. The mixture was cooled and water/organics distilled off under reduced pressure to a final distillation temperature of 100° C. On cooling a product of >90% mol purity was obtained.

What is claimed is:

1. A method for the production of vinyl phosphonic acid comprising hydrolysing vinyl phosphonic acid ester in the presence of a carbonyl compound.

2. A method according to claim 1, in which the carbonyl compound is a monofunctional aldehyde of general formula

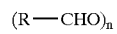

wherein R represents hydrogen or an alkyl group having from 1 to carbon atoms and n is a whole number of 1 or greater.

3. A method according to claim 2, in which the aldehyde is formaldehyde, paraformaldehyde or metaformaldehyde.

4. A method according to claim 2, in which the aldehyde is acetaldehyde.

5. A method according to claim 1, in which the carbonyl compound is a difunctional aldehyde of general formula

wherein n is zero or a whole number of from 1 to 4.

6. A method according to claim 5, in which the aldehyde is glyoxal.

7. A method according to claim 1, in which the carbonyl compound is a ketone of general formula:

wherein R$^1$ and R$^2$ (which may be the same or different) each represent an alkyl group having from 1 to 5 carbon atoms.

8. A method according to claim 7, in which the ketone is acetone.

9. A method according to claim 1, in which the carbonyl compound is a cycloalkyl ketone.

10. A method according to claim 9, in which the ketone is cyclohexanone.

11. A method according to claim 1, in which the ester is a bis(beta-haloalkyl) ester of vinyl phosphonic acid.

12. A method according to claim 11, in which the ester is the bis(betachloroethyl) ester of vinyl phosphonic acid.

13. A method according to claim 1, in which the carbonyl compound is present in an amount of from 1 to 250 mole % (with respect to the ester).

14. A method according to claim 13, in which the carbonyl compound is present in an amount of from 50 to 200 mole % (with respect to the ester).

15. A method according to claim 1, in which the hydrolysis is carried out at a temperature of about 140–150° C. and for a time of 30 to 40 hours.

16. A method according to claim 1, in which the hydrolysis is carried out at a pressure of from 1 to 10 atmospheres.

17. A method according to claim 16, in which the hydrolysis is carried out at a pressure of from 1 to 4 atmospheres.

18. A method according to claim 1, in which the hydrolysis is carried out under an inert atmosphere.

19. A method according to claim 18, in which the hydrolysis is carried out under nitrogen.

20. A method according to claim 1, in which the hydrolysis is carried out in the presence of an initial acid catalyst.

21. A method according to claim 20, in which the initial acid catalyst is sulphuric acid and is present in an amount of from 1 to 10 mole % (with respect to the ester).

22. A method according to claim 20, in which the initial acid catalyst comprises a heel of vinyl phosphonic acid.

* * * * *